(12) United States Patent
Liu et al.

(10) Patent No.: US 10,092,520 B2
(45) Date of Patent: Oct. 9, 2018

(54) COATING AGENT CONTAINING NANO-SIO$_2$ AND A PREPARATION METHOD THEREOF

(71) Applicant: GUANGDONG GUOFANG MEDICAL TECHNOLOGY CO., LTD., Dongguan (CN)

(72) Inventors: Ruiju Liu, Dongguan (CN); Yuyi Zhang, Dongguan (CN); Yang Yang, Dongguan (CN); Xuzhen Lu, Dongguan (CN); Li Chen, Dongguan (CN)

(73) Assignee: GUANGDONG GUOFANG MEDICAL TECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 15/539,985

(22) PCT Filed: Nov. 30, 2015

(86) PCT No.: PCT/CN2015/096048
§ 371 (c)(1),
(2) Date: Jun. 26, 2017

(87) PCT Pub. No.: WO2016/107361
PCT Pub. Date: Jul. 7, 2016

(65) Prior Publication Data
US 2017/0354608 A1    Dec. 14, 2017

(30) Foreign Application Priority Data
Dec. 31, 2014  (CN) .......................... 2014 1 0847291

(51) Int. Cl.
| | |
|---|---|
| *A61K 9/28* | (2006.01) |
| *A61K 47/02* | (2006.01) |
| *A61K 47/32* | (2006.01) |
| *A61K 47/38* | (2006.01) |
| *A61K 47/36* | (2006.01) |

(52) U.S. Cl.
CPC ............ *A61K 9/2806* (2013.01); *A61K 47/02* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2007/0292623 A1* | 12/2007 | Lin .......................... | C09D 1/00 427/407.1 |
| 2014/0106059 A1* | 4/2014 | Dave .................... | A61K 9/5073 427/2.14 |

OTHER PUBLICATIONS

Span and Tween, Croda Europe, 2018, pp. 1-6, (Year: 2018).*

* cited by examiner

*Primary Examiner* — Ernst V Arnold
*Assistant Examiner* — Kyung S Chang
(74) *Attorney, Agent, or Firm* — Ming Chow Sinorica, LLC

(57) ABSTRACT

The present invention relates to the technical field of coating agent, in particular to a coating agent containing nano-SiO$_2$ and a preparation method thereof. The coating agent consists of raw materials in parts by weight as follows: 50-60% film-forming agent, 5-10% plasticizing agent, 2-6% dispersing agent, 10-30% coloring agent, 15-20% antisticking agent and 2-5% nano-SiO$_2$. In the present invention, the nano-SiO$_2$, and the film-forming agent in the formulation can form a composite, which can enhance the property of coating agent, improve the coating film strength, and enhance the UV-protection and anti-discoloration functions, so as to improve the storage stability of drugs. The UV-protection and anti-discoloration functions of the coating agent prepared herein can be improved by more than 75%, and their film strength can be improved by more than 30%.

6 Claims, No Drawings

COATING AGENT CONTAINING NANO-SIO$_2$ AND A PREPARATION METHOD THEREOF

FIELD OF THE INVENTION

The present invention relates to the field of coating agent, in particular to a coating agent containing nano-SiO$_2$ and a preparation method thereof.

BACKGROUND OF THE INVENTION

Coating is one of the most important and cutting-edge processes of modern pharmacy. Under special equipment, the sugar or other film-forming materials are coated on the outer surface of pharmaceutical solid preparation according to particular process, to become one or several multi-functional protective layers with different thickness and flexibility tightly adhered to surface after drying; and this multi-functional protective layer is called coating.

For the oral dosage forms of pharmaceutically active compounds, such as tablets, in order to be given in the form of tablets, it is often required to mask the unpleasant taste of the pharmaceutically active compound, such as bitterness, besides, enhance the apparent properties of tablets, to make it easier to swallow and reduce the absorption of water or moisture. After the tablets absorb moisture, the activity of the pharmaceutically active ingredients may be decreased, or other adverse changes in the tablet structure may occur, or the appearance of the tablets is impaired. The film coating is a way of masking the taste. The film coating can be soluble in gastric juice, so it will not diminish the action of the pharmaceutically active compound, but have a sustained release effect.

Tablets, pills and granules are the three main dosage forms of pharmaceuticals. They are easy to use, easy to absorb and have good efficacy. However, these drugs are not stable during the storage and transportation; therefore, it is required to encapsulate coating agent on the surface of drugs. But the existing coating agents have low coating film strength, poor UV-protection and anti-discoloration functions, reducing the storage stability of drugs.

SUMMARY OF THE INVENTION

In order to overcome the shortcomings of the prior art, an object of the present invention is to provide a coating agent containing nano-SiO$_2$ and a preparation method thereof. The coating film of the coating agent containing nano-SiO$_2$ has high strength, excellent UV-protection and anti-discoloration functions, to enhance the storage stability. Its preparation method is simple, facilitating its promotion and applications.

The object of the invention is achieved through the following technical solutions.

A coating agent containing nano-SiO$_2$, comprising raw materials in parts by weight as follows:

| Film-forming agent | 50-60% |
| Plasticizing agent | 5-10% |
| Dispersing agent | 2-6% |
| Coloring agent | 10-30% |
| Antisticking agent | 15-20% |
| Nano-SiO$_2$ | 2-5%; | wherein the film-forming agent is one of HPMC, pregelatinized starch, polyvinyl alcohol (PVA), and polyacrylic resin or a mixture thereof;
wherein the plasticizing agent is one of PEG-400 (polyethylene glycol 400), triethyl citrate, triacetin, or a mixture thereof;
wherein the dispersing agent is Tween or Span or a mixture thereof;
wherein the coloring agent is one of pigment, titanium white powder, iron oxide or a mixture thereof;
wherein the antisticking agent is a pharmaceutically acceptable talcum powder.

Specifically, the particle size of the nano-SiO$_2$ is 20-80 nm.

Preferably, a coating agent containing nano-SiO$_2$, comprising raw materials in parts by weight as follows:

| Film-forming agent | 50-55% |
| Plasticizing agent | 5-8% |
| Dispersing agent | 3-5% |
| Coloring agent | 20-25% |
| Antisticking agent | 15-20% |
| nano-SiO$_2$ | 2-5%. | wherein the nano-SiO$_2$ is composed of two kinds of nano-SiO$_2$ with different particle sizes, the mass percentage of SiO$_2$ with particle size of 60-80 nm is 2-4%, and the mass percentage of SiO$_2$ with particle size of 20-30 nm is 1-2%.

Since the nano-SiO$_2$ particles with different sizes are added, the nano-SiO$_2$ particles with the size of 20-30 nm can be embedded in nano-SiO$_2$ particles with the size of 60-80 nm and between two nano-SiO$_2$ particles with the size of 60-80 nm, so that the nano-SiO$_2$ particles are connected more tightly, to enhance the film-forming property and achieve good coating effect.

Wherein, the film-forming agent is a mixture of HPMC, polyvinyl alcohol, pregelatinized starch in a mass ratio of 1:1:2.

Wherein, the film-forming agent is a mixture of pregelatinized starch, polyvinyl alcohol, polyacrylic resin in a mass ratio of 2:1:1.

Wherein, the plasticizing agent is a mixture of PEG-400 and triethyl citrate in a mass ratio of 2-3:1.

Wherein, the dispersing agent is a mixture of Tween and Span in a mass ratio of 2-3:1-2.

A method for preparing a coating agent containing nano-SiO$_2$, comprising the following steps:

Step (1): Take appropriate amount of plasticizing agent, dispersing agent and nano-SiO$_2$ to mix into nano-SiO$_2$ dispersion system under ultrasonic conditions for standby;

Step (2): Take appropriate amount of film-forming agent, coloring agent and antisticking agent to mix well, and under continuous mixing condition, spray the nano-SiO$_2$ dispersion system prepared in step (1) using an ultrasonic spray gun, and stir evenly to make nano-SiO$_2$ soft material;

Step (3): Sieve the above nano-SiO$_2$ soft material through a 20-mesh sieve to granulate; after vacuum drying of the wet granules at 55-60° C., crush them through 80-100 mesh, and then sieve through 80-100-mesh shaker, and sub-package them to get the finished product.

Wherein, the frequency of the ultrasonic wave is 20 to 25 kHz and the acoustic energy density is 0.3 w/ml according to the step (1).

Beneficial Effects of the Invention

In the present invention, the nano-SiO$_2$ and the film-forming agent in the formulation can form a composite, which can enhance the property of coating agent, improve the coating film strength, and enhance the UV-protection and anti-discoloration functions, so as to improve the storage stability of drugs. The film coating strength of the coating agent prepared in the invention is increased by more than 75%, and the UV-protection and anti-discoloration functions are increased by more than 30% compared with the traditional coating agent containing no nano-$SiO_2$.

An acceleration test of the coating agent containing nano-$SiO_2$ in the present invention is carried out under the condition of temperature of 40±1° C. and RH 75%; and it was found that, after storage for 6 months, the chromatic aberration (ΔE value) and the microbiological test data of the coating agent containing nano-$SiO_2$ have little differences from those stored for 0 month. When samples are reserved for testing under the condition of temperature of 25° C.±2° C. and RH60±10%, the chromatic aberration (ΔE value) and the microbiological test data of the coating agent containing nano-$SiO_2$ have little differences from those stored for 0 month. These results show that, the coating agents containing nano-$SiO_2$ in the present invention have strong storage stability and high tensile strength.

DETAILED DESCRIPTION OF THE EMBODIMENTS

The present invention is further described in combination with the following embodiments.

Example 1

A coating agent containing nano-$SiO_2$, comprising raw materials in parts by weight as follows: Film-forming agent 55%, plasticizing agent 8%, dispersing agent 5%, coloring agent 10%, antisticking agent 20%, and nano-$SiO_2$ 2%.

Wherein the particle size of nano-$SiO_2$ is 40 nm, the film-forming agent is a mixture of HPMC, polyvinyl alcohol, pregelatinized starch in a mass ratio of 1:1:2; the plasticizing agent is PEG-400; the dispersing agent is Tween; the coloring agent is pigment; the antisticking agent is pharmaceutically acceptable talcum powder.

A method for preparing a coating agent containing nano-$SiO_2$, comprising the following steps:
Step (1): Take appropriate amount of plasticizing agent, dispersing agent and nano-$SiO_2$ to mix into nano-$SiO_2$ dispersion system under ultrasonic conditions; and the frequency of the ultrasonic wave is 20 kHz and the acoustic energy density is 0.3 w/ml, for standby;
Step (2): Take appropriate amount of film-forming agent, coloring agent and antisticking agent to mix well, and under continuous mixing condition, spray the nano-$SiO_2$ dispersion system prepared in step (1) using an ultrasonic spray gun, and stir evenly to make nano-$SiO_2$ soft material;
Step (3): Sieve the above nano-$SiO_2$ soft material through a 20-mesh sieve to granulate; after vacuum drying of the wet granules at 55° C., crush them through 80 mesh, and then sieve through 80-mesh shaker, and sub-package them to get the finished product.

The film coating strength of the coating agent prepared in this embodiment is increased by 75.2%; and the UV-protection and anti-discoloration functions are increased by 30.6%.

Example 2

A coating agent containing nano-$SiO_2$, comprising raw materials in parts by weight as follows:
Film-forming agent 60%, plasticizing agent 5%, dispersing agent 2%, coloring agent 15%, antisticking agent 15% and nano-$SiO_2$ 3%.

Wherein the particle size of nano-$SiO_2$ is 60 nm, the film-forming agent is a mixture of pregelatinized starch, polyvinyl alcohol, polyacrylic resin in a mass ratio of 2:1:1; the plasticizing agent is a mixture of triethyl citrate and triacetin in a mass ratio of 1:1; the dispersing agent is Span; the coloring agent is titanium white powder; the antisticking agent is pharmaceutically acceptable talcum powder.

A method for preparing a coating agent containing nano-$SiO_2$, comprising the following steps:
Step (1): Take appropriate amount of plasticizing agent, dispersing agent and nano-$SiO_2$ to mix into nano-$SiO_2$ dispersion system under ultrasonic conditions; and the frequency of the ultrasonic wave is 22 kHz and the acoustic energy density is 0.3 w/ml, for standby;
Step (2): Take appropriate amount of film-forming agent, coloring agent and antisticking agent to mix well, and under continuous mixing condition, spray the nano-$SiO_2$ dispersion system prepared in step (1) using an ultrasonic spray gun, and stir evenly to make nano-$SiO_2$ soft material;
Step (3): Sieve the above nano-$SiO_2$ soft material through a 20-mesh sieve to granulate; after vacuum drying of the wet granules at 58° C., crush them through 90 mesh, and then sieve through 90-mesh shaker, and sub-package them to get the finished product.

The film coating strength of the coating agent prepared in this embodiment is increased by 78.6%; and the UV-protection and anti-discoloration functions are increased by 35.2%.

Example 3

A coating agent containing nano-$SiO_2$, comprising raw materials in parts by weight as follows: Film-forming agent 53%, plasticizing agent 7%, dispersing agent 4%, coloring agent 14%, antisticking agent 17%, and nano-$SiO_2$ 5%.

Wherein the particle size of nano-$SiO_2$ is 80 nm, the film-forming agent is a pregelatinized starch; the plasticizing agent is a mixture of PEG-400 and triethyl citrate in a mass ratio of 2:1; the dispersing agent is a mixture of Tween and Span in a mass ratio of 2:1; the coloring agent is iron oxide; and the antisticking agent is pharmaceutically acceptable talcum powder.

A method for preparing a coating agent containing nano-$SiO_2$, comprising the following steps:
Step (1): Take appropriate amount of plasticizing agent, dispersing agent and nano-$SiO_2$ to mix into nano-$SiO_2$ dispersion system under ultrasonic conditions; and the frequency of the ultrasonic wave is 25 kHz and the acoustic energy density is 0.3 w/ml, for standby;
Step (2): Take appropriate amount of film-forming agent, coloring agent and antisticking agent to mix well, and under continuous mixing condition, spray the nano-$SiO_2$ dispersion system prepared in step (1) using an ultrasonic spray gun, and stir evenly to make nano-$SiO_2$ soft material;
Step (3): Sieve the above nano-$SiO_2$ soft material through a 20-mesh sieve to granulate; after vacuum drying of the wet granules at 60° C., crush them through 100 mesh, and then sieve through 100-mesh shaker, and sub-package them to get the finished product.

The film coating strength of the coating agent prepared in this embodiment is increased by 80.1%; and the UV-protection and anti-discoloration functions are increased by 35.8%.

Example 4

A coating agent containing nano-SiO$_2$, comprising raw materials in parts by weight as follow:
Film-forming agent 50%, plasticizing agent 6%, dispersing agent 3%, coloring agent 22%, antisticking agent 15%, nano-SiO$_2$ 4%; of which, 3% of the nano-SiO$_2$ with the particle size of 60 nm and 1% of the nano-SiO$_2$ with the particle size of 20 nm.

Wherein the film forming agent is a mixture of pregelatinized starch and polyacrylic resin in a mass ratio of 2:1; the plasticizing agent is a mixture of PEG-400 and triethyl citrate in a mass ratio of 3:1; the dispersing agent is a mixture of Tween and Span in a mass ratio of 3:1; the coloring agent is a mixture of titanium white powder and iron oxide in a mass ratio of 1:2; the antisticking agent is pharmaceutically acceptable talcum powder.

Other contents in this embodiment are the same as those in Example 1.

The film coating strength of the coating agent prepared in this embodiment is increased by 83.5%; and the UV-protection and anti-discoloration functions are increased by 45.6%.

Example 5

A coating agent containing nano-SiO$_2$, comprising raw materials in parts by weight as follow:
Film-forming agent 51%, plasticizing agent 6%, dispersing agent 3%, coloring agent 21%, antisticking agent 16%, nano-SiO$_2$ 3%; of which, 2% of the nano-SiO$_2$ with the particle size of 80 nm and 1% of the nano-SiO$_2$ with the particle size of 30 nm.

Wherein the film-forming agent is a mixture of pregelatinized starch and polyvinyl alcohol in a mass ratio of 3:1; the film-forming agent is a mixture of pregelatinized starch, polyvinyl alcohol and polyacrylic resin in a mass ratio of 2:1:1; the plasticizing agent is triethyl citrate; the dispersing agent is a mixture of Tween and Span in a mass ratio of 3:2; the coloring agent is a mixture of pigment and iron oxide in a mass ratio of 2:1; and the antisticking agent is pharmaceutically acceptable talcum powder.

Other contents in this embodiment are the same as those in Example 2.

The film coating strength of the coating agent prepared in this embodiment is increased by 84.5%; and the UV-protection and anti-discoloration functions are increased by 48%.

Example 6

A coating agent containing nano-SiO$_2$, comprising raw materials in parts by weight as follow:
Film-forming agent 52%, plasticizing agent 5%, dispersing agent 2%, coloring agent 20%, antisticking agent 18%, nano-SiO$_2$ 3%; of which, 2% of the nano-SiO$_2$ with the particle size of 70 nm and 1% of the nano-SiO$_2$ with the particle size of 25 nm.

Wherein the film forming agent is a mixture of HPMC, pregelatinized starch and polyacrylic resin in a mass ratio of 1:2:1; the plasticizing agent is a mixture of PEG-400 and triacetin in a mass ratio of 2:1; The dispersing agent is a mixture of Tween and Span in a mass ratio of 1:1; the coloring agent is iron oxide; the antisticking agent is pharmaceutically acceptable talcum powder.

Other contents in this embodiment are the same as those in Example 3.

The film coating strength of the coating agent prepared in this embodiment is increased by 85%; and the UV-protection and anti-discoloration functions are increased by 49.8%.

Following is a description about the determination of technical parameters of the product in the invention.

The coating agent containing nano-SiO$_2$ in the invention is made by safe and non-toxic medicinal materials. It not only has the characteristics of ordinary coating premix, but also has the advantages of small dosage, delicate film-forming, high gloss, anti-discoloration and self-cleaning effects, so as to achieve the purpose of TCM coating, with high product stability and long shelf life.

In order to demonstrate that this product is superior to the coating agent containing no nano-material, an 6-month acceleration test is carried out for two kinds of coating materials according to proposed packaging on the markets. Samples are reserved naturally for 12 months at room temperature for regular sampling, to compare the key items. Testing is carried out according to the relevant provisions in Chinese Pharmacopoeia (2010 Edition).

Acceleration Test
Test conditions: temperature 40±1° C., RH75%
Sample packaging: PVC bags
Source: Provided by R & D Center of the Company
Batch No.: (containing nano-SiO$_2$) 20130701A, (containing no nano-SiO$_2$) 20130701B
Duration: from Jul. 15, 2013 to Jan. 15, 2014
Test item: tensile strength, chromatic aberration (ΔE value)
Test method: six batches of samples (3 batches of coating agent containing nano-SiO2 and 3 batches of coating agent containing no nano-SiO$_2$) were placed to closed containers with saturated sodium chloride solution (RH75%) at the bottom, and then placed to an incubator at 40±1° C. for 6 months; samples were taken regularly at Months 0, 1, 2, 3 and 6. Testing was carried out according to the relevant provisions in Chinese Pharmacopoeia (2010 Edition), the results were shown in Table 1.

TABLE 1

Acceleration test of coating agent containing nano-SiO$_2$

| Batch No. | Sampling Time | Duration of storage (month) | Chromatic aberration (ΔE value) | Tensile strength (N · cm-2) |
|---|---|---|---|---|
| 20130701A | Jul. 15, 2013 | 0 | 0 | 376 |
| | Aug. 5, 2013 | 1 | 0 | 371 |
| | Sep. 15, 2013 | 2 | 0.2 | 365 |
| | Oct. 15, 2013 | 3 | 0.3 | 360 |
| | Jan. 15, 2014 | 6 | 0.5 | 350 |

As shown from Table 1, compared with that in Month 0, the chromatic aberration of coating agent containing nano-SiO$_2$ in the present invention in Months 1 to 6 showed slight changes, and the tensile strength was high.

TABLE 2

Acceleration test of coating agent containing no nano-SiO$_2$

| Batch No. | Sampling Time | Duration of storage (month) | Chromatic aberration (ΔE value) | Tensile strength (N · cm-2) |
|---|---|---|---|---|
| 20130701A | Jul. 15, 2013 | 0 | 0 | 285 |
| | Aug. 5, 2013 | 1 | 0.6 | 278 |
| | Sep. 15, 2013 | 2 | 0.9 | 266 |

TABLE 2-continued

Acceleration test of coating agent containing no nano-SiO$_2$

| Batch No. | Sampling Time | Duration of storage (month) | Chromatic aberration (ΔE value) | Tensile strength (N · cm−2) |
|---|---|---|---|---|
| | Oct. 15, 2013 | 3 | 1.6 | 241 |
| | Jan. 15, 2014 | 6 | 2.8 | 228 |

As shown from Table 2, compared with that in Month 0, the chromatic aberration of coating agent containing no nano-SiO$_2$ in Months 1 to 6 showed great changes, and the tensile strength was low.

(II) Sample Reservation Test at Room Temperature
Test conditions: placed at room temperature (temperature 25° C.±2° C., RH60±10%)
Sample packaging: PVC bags
Source: Provided by R & D Center of the Company
Batch No.: (containing nano-SiO$_2$) 20130701A,
(containing no nano-SiO$_2$) 20130701B
Duration: from Jul. 15, 2013 to Jul. 15, 2014
Test items: tensile strength, chromatic aberration (ΔE value)
Test method: six batches of samples (3 batches of coating agent containing nano-SiO$_2$ and 3 batches of coating agent containing no nano-SiO$_2$) were placed at room temperature; samples were taken regularly at Months 0, 3, 6, 9, 12. Testing was carried out according to the relevant provisions in Chinese Pharmacopoeia (2010 Edition), the results were shown in Tables 3 and 4.

TABLE 3

Room temperature test of coating agent containing nano-SiO$_2$

| Batch No. | Sampling Time | Duration of storage (month) | Chromatic aberration (ΔE value) | Tensile strength (N · cm−2) |
|---|---|---|---|---|
| 20130701A | Jul. 15, 2013 | 0 | 0 | 376 |
| | Oct. 5, 2013 | 3 | 0.1 | 372 |
| | Jan. 15, 2014 | 6 | 0.1 | 368 |
| | Apr. 15, 2014 | 9 | 0.2 | 364 |
| | Jul. 15, 2014 | 12 | 0.4 | 361 |

As shown from Table 3, compared with that in Month 0, the chromatic aberration of coating agent containing nano-SiO$_2$ in the present invention in Months 1 to 12 showed slight changes, and the tensile strength was high.

TABLE 4

Room temperature test of coating agent containing no nano-SiO$_2$

| Batch No. | Sampling Time | Duration of storage (month) | Chromatic aberration (ΔE value) | Tensile strength (N · cm−2) |
|---|---|---|---|---|
| 20130701B | Jul. 15, 2013 | 0 | 0 | 285 |
| | Oct. 5, 2013 | 3 | 0.5 | 276 |
| | Jan. 15, 2014 | 6 | 0.8 | 265 |
| | Apr. 15, 2014 | 9 | 1.1 | 247 |
| | Jul. 15, 2014 | 12 | 1.9 | 238 |

As shown from Table 4, compared with that in Month 0, the chromatic aberration of coating agent containing no nano-SiO$_2$ in Months 1 to 12 showed great changes, and the tensile strength was low.

(3) CONCLUSIONS

After the performance tests on coating agent containing nano-SiO$_2$ and coating agent containing no nano-SiO$_2$ and combing with the analysis in Tables 1, 2, 3 and 4, the chromatic aberration of coating agent containing nano-SiO$_2$ showed basically no change compared with that in Month 0, while the chromatic aberration of coating agent containing no nano-SiO$_2$ showed great change compared with that in Month 0. The tensile strengths of coating agent containing nano-SiO$_2$ in both the acceleration test and room temperature test were significantly higher than those of coating agent containing no nano-SiO$_2$. Results showed that the coating agent containing nano-SiO$_2$ has strong superiority.

It should be noted that the above embodiments are merely illustrative of the technical solutions of the present invention and are not to be construed as limiting the scope of the invention, and although the present invention has been described in detail with reference to preferred embodiments, ordinary technicians skilled in the art should understand that technical solutions of the present invention may be modified or equivalently replaced without departing from the essence and scope of the technical solutions of the present invention.

What is claimed is:

1. A coating agent containing nano-SiO$_2$, comprising raw materials in parts by weight as follows:

| Film-forming agent | 50-60% |
|---|---|
| Plasticizing agent | 5-10% |
| Dispersing agent | 2-6% |
| Coloring agent | 10-30% |
| Antisticking agent | 15-20% |
| Nano-SiO$_2$ | 23-5%; | wherein the film-forming agent is a mixture of hydroxypropyl methylcellulose (HPMC), polyvinyl alcohol, and pregelatinized starch in a mass ratio of 1:1:2, or the film-forming agent is a mixture of pregelatinized starch, polyvinyl alcohol, and polyacrylic resin in a mass ratio of 2:1:1;
wherein the plasticizing agent is one of polyethylene glycol-400 (PEG-400), triethyl citrate, triacetin, or a mixture thereof;
wherein the dispersing agent is polyethoxylated sorbitan ester (Tween) or sorbitan ester (Span) or a mixture thereof;
wherein the coloring agent is one of pigment, titanium white powder, iron oxide or a mixture thereof;
wherein the antisticking agent is a pharmaceutically acceptable talcum powder; and
wherein the nano-SiO$_2$ is composed of two different nano-SiO$_2$ with different particle sizes, the mass percentage of the first SiO$_2$ with a particle size of 60-80 nm is 2-4%, and the mass percentage of the second SiO$_2$ with a particle size of 20-30 nm is 1-2%.

2. The coating agent containing nano-SiO$_2$ according to claim 1, wherein it comprises raw materials in parts by weight as follows:

| Film-forming agent | 50-55% |
|---|---|
| Plasticizing agent | 5-8% |
| Dispersing agent | 3-5% |
| Coloring agent | 20-25% |
| Antisticking agent | 15-20% |
| Nano-SiO$_2$ | 3-5%. |

3. The coating agent containing nano-SiO$_2$ according to claim 1, wherein the plasticizing agent is a mixture of polyethylene glycol (PEG-400) and triethyl citrate in a mass ratio of 2-3:1.

4. The coating agent containing nano-SiO$_2$ according to claim 1, wherein the dispersing agent is a mixture of is polyethoxylated sorbitan ester (Tween) or sorbitan ester (Span) in a mass ratio of 2-3:1-2.

5. A method for preparing the coating agent containing nano-SiO$_2$ according claim 1, comprising the following steps:

Step (1): Take appropriate amount of plasticizing agent, dispersing agent and nano-SiO$_2$ to mix into nano-SiO$_2$ dispersion system under ultrasonic conditions for standby;

Step (2): Take appropriate amount of film-forming agent, coloring agent and antisticking agent to mix well, and under continuous mixing condition, spray the nano-SiO$_2$ dispersion system prepared in step (1) using an ultrasonic spray gun, and stir evenly to make nano-SiO$_2$ soft material;

Step (3): Sieve the above nano-SiO$_2$ soft material through a 20-mesh sieve to granulate; after vacuum drying of the wet granules at 55-60° C., crush them through 80-100 mesh, and then sieve through 80-100-mesh shaker, and sub-package them to get the finished product.

6. The method for preparing a coating agent containing nano-SiO$_2$ according to claim 5, wherein the frequency of the ultrasonic wave is 20 to 25 kHz and the acoustic energy density is 0.3 w/ml according to step (1).

* * * * *